United States Patent
Lu et al.

(10) Patent No.: US 11,065,099 B2
(45) Date of Patent: Jul. 20, 2021

(54) FLEXIBLE HOLLOW LUMEN COMPOSITE

(71) Applicant: THE SECANT GROUP, LLC, Telford, PA (US)

(72) Inventors: Steven Lu, Ambler, PA (US); Peter D. Gabriele, Frisco, TX (US); Jeremy J. Harris, Doylestown, PA (US); Seth A. Winner, Durham, NC (US); Andrew Metzger, Lafayette Hill, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 242 days.

(21) Appl. No.: 16/153,219

(22) Filed: Oct. 5, 2018

(65) Prior Publication Data

US 2019/0105148 A1 Apr. 11, 2019

Related U.S. Application Data (60) Provisional application No. 62/569,086, filed on Oct. 6, 2017.

(51) Int. Cl.
*A61F 2/07* (2013.01)
*A61L 27/50* (2006.01)
(Continued)

(52) U.S. Cl.
CPC .............. *A61F 2/07* (2013.01); *A61L 27/48* (2013.01); *A61L 27/50* (2013.01); *A61L 27/507* (2013.01); *A61L 27/58* (2013.01); *A61L 31/06* (2013.01); *A61L 31/12* (2013.01); *A61L 31/129* (2013.01); *A61L 31/14* (2013.01); *A61L 31/148* (2013.01); *A61F 2002/072* (2013.01); *A61F 2210/0004* (2013.01); *A61F 2240/001* (2013.01); *A61F 2250/0067* (2013.01); *A61F 2250/0069* (2013.01); *A61L 2430/32* (2013.01);
(Continued)

(58) Field of Classification Search
CPC ............................ A61F 2/07; A61F 2002/072
See application file for complete search history.

(56) References Cited

U.S. PATENT DOCUMENTS

| | | | |
|---|---|---|---|
| 6,017,566 | A | 1/2000 | Bunczek et al. |
| 6,217,609 | B1 | 4/2001 | Haverkost |

(Continued)

FOREIGN PATENT DOCUMENTS

| | | |
|---|---|---|
| WO | 2014074134 A1 | 5/2014 |
| WO | 2017143075 A1 | 8/2017 |

OTHER PUBLICATIONS

Allen et al., "Nerve regeneration and elastin formation within poly(glycerol sebacate)-based synthetic arterial grafts one-year post-implantation in a rat model", Biomaterials, vol. 35, pp. 165-173, (2014).

(Continued)

*Primary Examiner* — Jason-Dennis N Stewart
(74) *Attorney, Agent, or Firm* — McNees Wallace & Nurick LLC (57) ABSTRACT

A composite lumen includes an extruded tube of a composite including a poly(glycerol sebacate) (PGS) matrix mixed with a PGS thermoset filler. The composite lumen also includes an overbraid structure overlying an outer surface of the extruded tube. A method of forming a composite lumen includes extruding a PGS tube of a composite including a PGS matrix mixed with a PGS thermoset filler. The method also includes applying an overbraid structure over an outer surface of the extruded tube.

17 Claims, 5 Drawing Sheets

(51) Int. Cl.
  *A61L 27/58*    (2006.01)
  *A61L 31/14*    (2006.01)
  *A61L 27/48*    (2006.01)
  *A61L 31/12*    (2006.01)
  *A61L 31/06*    (2006.01)
  *B29D 23/00*    (2006.01)
  *B29K 71/00*    (2006.01)
  *B29K 467/00*   (2006.01)
  *B29L 31/00*    (2006.01)

(52) U.S. Cl.
  CPC .......... *B29D 23/00* (2013.01); *B29K 2071/02* (2013.01); *B29K 2467/04* (2013.01); *B29L 2031/7534* (2013.01)

(56) References Cited

U.S. PATENT DOCUMENTS

| | | |
|---|---|---|
| 6,444,782 B1 | 9/2002 | Hamlin |
| 7,722,894 B2 | 5/2010 | Wang et al. |
| 8,192,348 B2 | 6/2012 | Tranquillo et al. |
| 8,716,410 B2 | 5/2014 | Venkatraman et al. |
| 2002/0087176 A1 | 7/2002 | Greenhalgh |
| 2004/0039440 A1 | 2/2004 | Elmaleh |
| 2005/0133046 A1 | 6/2005 | Becker et al. |
| 2005/0169958 A1 | 8/2005 | Hunter et al. |
| 2006/0009839 A1 | 1/2006 | Tan et al. |
| 2007/0023974 A1 | 2/2007 | Wu |
| 2009/0082840 A1 | 3/2009 | Rusk et al. |
| 2009/0214373 A1 | 8/2009 | Stinson et al. |
| 2010/0094404 A1 | 4/2010 | Greenhalgh et al. |
| 2014/0309726 A1 | 10/2014 | Wang |
| 2015/0320542 A1 | 11/2015 | Gabriele et al. |
| 2016/0242895 A1 | 8/2016 | Matheny |
| 2017/0246316 A1 | 8/2017 | Wroblesky et al. |

OTHER PUBLICATIONS

Chen et al., "Characterisation of a soft elastomer poly(glycerol sebacate) designed to match the mechanical properties of myocardial tissue", Biomaterials, vol. 29, pp. 47-57, (2008).

Gao et al., "Macroporous Elastomeric Scaffolds with Extensive Micropores for Soft Tissue Engineering", Tissue Engineering, vol. 12, pp. 917-925, (2006).

Guo et al., "Characterization and optimization of glycerol/sebacate ratio in poly(glycerol-sebacate elastomer for cell culture application", J. Biomed. Mater. Res. Part A, vol. 102A, pp. 3903-3907, (2014).

Jaafar et al., "Spectroscopic evaluation, thermal, and thermomechanical characterization of poly(glycerol-sebacate) with variations in curing temperatures and durations", J. Mater. Sci., vol. 45, pp. 2525-2529, (2010).

Pryor et al., "Poly(glycerol sebacate) films prevent postoperative adhesions and allow laparoscopic placement", Surgery, vol. 146, pp. 490-497, (2009).

Sun et al., "The influence of lactic acid on the properties of Poly (glycerol-sebacate-lactic acid)", Materials Science and Engineering C, vol. 29, pp. 178-182, (2009).

Wang et al., "A Tough Biodegradable Elastomer", Nature Biotechnology, vol. 20, pp. 602-606, (2002).

FLEXIBLE HOLLOW LUMEN COMPOSITE

CROSS-REFERENCE TO RELATED APPLICATIONS

This application claims priority to and the benefit of U.S. Provisional Application No. 62/569,086 filed Oct. 6, 2017, which is hereby incorporated by reference in its entirety.

FIELD OF THE INVENTION

The present invention relates to the field of implantable lumens, such as, for example, grafts to replace blood vessels. More specifically, the present invention is related to flexible hollow lumen composites.

BACKGROUND

Cardiovascular disease is the leading cause of death worldwide. Although drug treatment of cardiovascular disease is increasing, two of the primary methodologies currently used to treat cardiovascular disease are coronary artery bypass grafts and percutaneous coronary intervention, commonly referred to as angioplasty.

During an angioplasty procedure, a stent is often implanted into a restricted blood vessel to open the diameter of the blood vessel. Various types of stents are currently known for such procedures. Each type of stent has certain advantages, but each type also suffers from one or more known complications or weaknesses, which may include, but are not limited to, restenosis, the need for long term use of anticoagulants, inhibition of natural blood vessel motion (such as pulsatile motion), in-stent thrombosis, improper healing, and potential for fracture of the stent.

In contrast to percutaneous coronary intervention, a coronary artery bypass graft is implanted to bypass a blockage or obstruction in a coronary artery. Various types of grafts have been used for bypass surgeries, including biological grafts (e.g. autografts, allografts and xenografts) and artificial grafts (e.g. polytetrafluoroethylene (PTFE), expanded PTFE (ePTFE), and poly(ethylene terephthalate) (PET)). Additionally, although not widely used, tissue-engineered grafts are being developed in which the graft is produced in vitro.

Although each of the known grafts has certain advantages, such as low cost, high availability, or similarity to native tissue, each of the known grafts also suffers from one or more known complications or weakness. For instance, while autografts are the current gold standard because of their high durability, the lack of availability and donor site morbidity continue to be issues. Allografts typically take longer to integrate into the body and require extensive processing before they are suitable for implantation. Artificial grafts are readily available but may be more prone to infection, thrombosis, or intimal hyperplasia and may require long term use of medication, such as anticoagulants. Although tissue-engineered grafts overcome many of the problems associated with commonly-used biological and artificial grafts, tissue-engineered grafts are extremely expensive and take a long time to manufacture.

In general, native vessels remain the preferred choice for revascularization procedures, however, such tissues are not always available. In such cases, synthetic materials, such as expanded polytetrafluoroethylene (ePTFE) and poly(ethylene terephthalate) (PET), have been used successfully as vascular conduits when the graft diameter exceeds 6 mm. Results have been poor, however, with grafts less than 6 mm in diameter, due to the development of thrombi and intimal hyperplasia.

The use of textile technology to make three-dimensional hollow lumen structures is a well-known art. While flexible, water-impermeable lumens are described in U.S. Pat. App. Pub. No. 2015/0320542 (incorporated herein by reference) and work well, continued improvements are still desirable to further enhance the performance of such devices.

BRIEF DESCRIPTION OF THE INVENTION

In some embodiments, a composite lumen includes an extruded tube of a composite including a poly(glycerol sebacate) (PGS) matrix mixed with a PGS thermoset filler. The composite lumen also includes an overbraid structure overlying an outer surface of the extruded tube.

In some embodiments, a method of forming a composite lumen includes extruding a poly(glycerol sebacate) (PGS) tube of a composite including a PGS matrix mixed with a PGS thermoset filler. The method also includes applying an overbraid structure over an outer surface of the extruded tube.

Exemplary embodiments are directed to flexible composite braids, composite braids formed from such processes, the composition of a textile and elastic sealer which includes the composite braid, and the use of these composite braids for the repair and regeneration of tubular tissues for grafts and other applications to replace diseased or damaged tissue vessels.

Exemplary embodiments provide a degradable endogenous graft (DEG) including a luminal composite of a textile engineered braided structure, embedded or encapsulated with an elastic biodegradable polymer infusion coating comprising poly(glycerol-sebacate) (PGS) that enhances biomimetic elastomeric properties, provides mechanobiological tissue compliance, and that remains flexible and blood/water-impermeable to allow cardiovascular tissue to replace said composite in vivo.

A specified range and combination of different braiding parameters and sealing parameters may be tuned to fit a variety of reparative and regenerative applications for luminal tissues depending upon a particular application.

A patient with chronic cardiovascular disease may eventually run out of autograft transplant options or may not be of such required health to survive the trauma of harvesting autologous vascular tissues. Having an option to use a DEG prosthesis that offers the patient immediate selection and quality of care in an emergency is both life-saving and economical.

Exemplary embodiments provide a luminal composite that acts as an in vivo resorbable scaffold structure that replaces diseased or degenerated vascular structures via endogenous regeneration of the luminal vascular anatomy. Such a composite provides a vascular structure that can be stored without extensive biologic storage logistics or conditions and provides the surgeon with an off-the-shelf patient-ready regenerative prosthesis.

Furthermore, exemplary embodiments do not require preconditioning or incorporation of active pharmaceuticals or biologic growth or trophic factors to establish tissue residence and differentiation into the final tissue anatomy and physiology.

Various features and advantages of the present invention will be apparent from the following more detailed descrip-

BRIEF DESCRIPTION OF THE DRAWINGS

Wherever possible, the same reference numbers will be used throughout the drawings to represent the same parts.

DETAILED DESCRIPTION OF THE INVENTION

A major advantage of a braid-based technology over knitting or weaving is in the engineering properties associated with the braided construct. The braided construct may bio-mimic mimic mechanobiological features such as foreshortening and elongation, radial distension to provide pulsatile mechanics in a hemodynamic environment, kink-resistant vascular characteristics, and an anatomically-correct long-axis profile similar to actual arterial and venous anatomy (arterial vascular structures naturally diminish bore-diameter as a function of distance from the heart for arteries whereas venous vascular structures naturally expand their bore diameter from the most distal vascular/capillary location returning to the heart). In some embodiments, a braid mandrel is configured to simulate the natural diminishing bore diameter during manufacture, providing a more realistic hemodynamic structure in the finished braided lumen.

The structure of woven tubes may have very low water permeability but lends them little flexibility and kink resistance without corrugation processing. Knitted tubes have very high flexibility but may be structurally weak and have high water permeability. Luminal structures that are braided offer high flexibility and kink resistance and may maintain their circular morphology through compression and tension, both axially and radially. Although textile braids may be manufactured with low water permeability, it comes at a cost to their flexibility.

Figure 1:
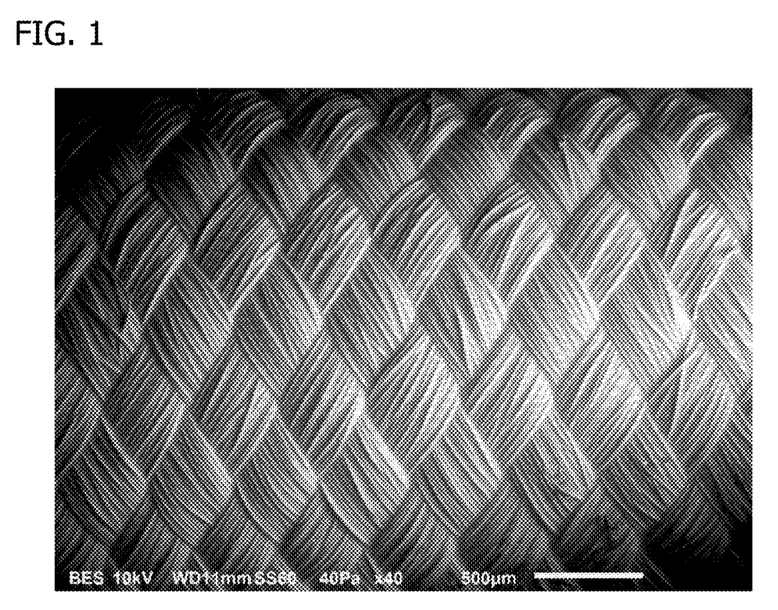
FIG. 1 shows a braid structure of a lumen in accordance with an exemplary embodiment coated with an elastic sealer.
Figure 2:
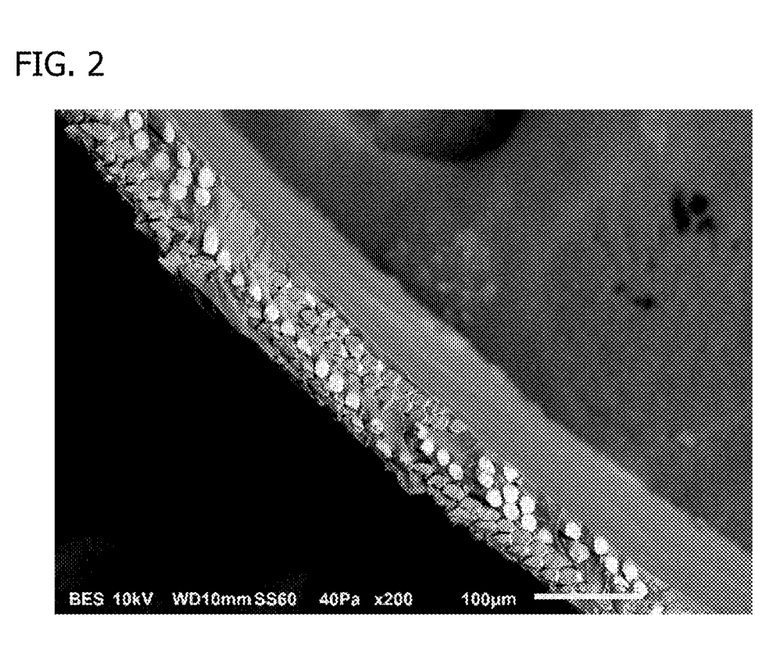
FIG. 2 shows a cross-section of a braid structure of a lumen in accordance with an exemplary embodiment infused with an elastic sealer.

Exemplary embodiments provide highly flexible braids that are infusion coated with an elastic sealer to make kink-resistant, water-impermeable composite braids as illustrated in FIG. 1 and FIG. 2. The interlacing pattern of the braids is visible in FIG. 1. The penetration of the coating between the braids is visible in FIG. 2.

Variations in yarn thickness, yarn density, yarn tension, porosities, braid angle, and braiding patterns are employed to form a braided structure suitable for exemplary embodiments that, when combined with infusion of an elastic material, seals the interstitial spaces between fibers with varying amounts of elastic material that create a water-impermeable wall. Thus, infusing creates an embedded coating that encapsulates the fibrils. Specific combinations of braiding and infusion-coating parameters may yield a variety of composite braids with different levels of flexibility and water permeability.

The uniformity of the PGS (as used herein, PGS includes both neat PGS and PGS copolymers, such as, for example, PGS-urethane (PGSU)) infusion coating provides many engineering features to the 'naked' braid that otherwise would not be expected. The infusion of the elastomeric PGS polymer into the braid-lattice embeds the individual fibers of the yarn, providing a cohesive and uniform strength, matrix energy transfer and dissipation, and memory for recovery during radial distention. This action resulting from the embedding minimizes fiber-to-fiber friction and maximizes kinetic energy dissipation important in a continuously-active in vivo structure.

Exemplary embodiments achieve a uniform infusion that provides a level of strength to elongation that would otherwise fail to yield to above-normal physical tension or internal hemodynamic pressure. Uniform PGS infusion also provides 'trimability' to eliminate fiber fraying.

The ability to create composite braids with different characteristics allows the building of constructs that can match the physical properties of luminal tissues that the composite braid is intended to repair and/or regenerate.

A presently-preferred embodiment employs a maypole braid made from polyglycolide (PGA) yarn and subsequently infusion coated in poly(glycerol sebacate) (PGS). One advantage of using PGS as an elastic infusible sealer/coating is its anti-microbial, non-inflammatory, non-immunogenic, and non-thrombogenic properties. By using PGS as a degradable elastic infusion sealer-coating, the acute physiological response towards the composite braid may be modulated to influence a post-implantation mechanobiological healing response. Although discussed primarily with respect to PGA braids and PGS infusion coatings, other biodegradable yarns (e.g., polylactide (PLA), poly(lactic-co-glycolic acid) (PLGA), polycaprolactone (PCL), polydioxanone (PDO), poly(trimethylene carbonate) (PTC), or PGSU) may be used, as may other biodegradable elastomers (e.g., polyurethane (PU) or PGSU) be used for the infusion coating.

Particular combinations of braiding and infusion coating parameters allow for a flexible (i.e., small kink radius) and water-impermeable anatomically-similar luminal construct.

To create flexible and water-impermeable braids of different diameters, both braiding and infusion coating parameters need to be adjusted to tune wall thickness, braid density, and % PGS mass. Wall thickness is influenced by yarn denier, ply, picks per inch (PPI), and ply twist. Braid density is influenced by yarn denier, PPI, ply, and number of ends. % PGS mass is influenced by the infusion coating method, infusion coating solution concentration, braid density, and wall thickness.

Braid stiffness or suppleness may also be influenced by thermal annealing to modulate crystallinity. Crystallinity imparted by thermal annealing may be affected by braiding and yarn tension, as well as by the degradation profile.

Degradation of the composite lumen formed by the resorbable textile and resorbable elastic infused sealer may be tuned by the amount of textile, filament size, and included elastomer (e.g., braid density, denier/filament, or % PGS mass). Thermal annealing to impart crystallinity into the textile structure may also be modified to tune the degradation rate of the textile braid. By having the ability to modify the degradation rate of the composite braid, the composite braid may be tuned to match the formation of neotissue in regenerative applications. By matching the degradation and healing rates, issues such as loss of mechanical integrity and/or stress-shielding may be prevented.

Exemplary embodiments are particularly useful for construction of small-bore lumens to replace vessels having an inner diameter of 6 mm or less, such as those as small as 3 mm. In some embodiments, the construction of a small bore vessel having an inner diameter of 3 mm is formed by providing a braid with a braid angle greater than 100°, a wall thickness to inner diameter ratio greater than 0.02, picks per inch (PPI) from between about 25 and about 135, number of ends between about 12 and about 48, with a braid pattern that is selected from 1×1, 2×2, or 2×1 and with an effective yarn denier (defined as yarn denier×ply number) greater than 45.

A presently-preferred embodiment has a braid angle in the range of 110 to 135, such as 120 to 130, a wall thickness to inner diameter ratio is in the range of 0.03 to 0.07, such as 0.05 to 0.07, PPI in the range of 50 to 120, such as 50 to 80, 24 ends, a 1×1 braid pattern, and effective yarn denier in the range of 180 to 360.

The infusion coating with the elastic material may be accomplished by dip coating, spray coating, and/or primed by wetting the yarn with the solvent prior to coating. Infusion may be optimized using high-pressure coating or injection technology such as that used to make reinforced high-performance hoses for harsh environments.

The infusion coating may vary by solids or viscosity and may be augmented with additives to enhance yarn fibril wetting for encapsulation and embedding.

The use of infusion technology achieves a uniformity in the PGS infusion coating and unexpectedly achieves better results that otherwise would not be expected. The infusion of the elastomeric PGS polymer into the braid-lattice embeds the individual fibers of the yarn, thereby providing a cohesive and uniform strength, matrix energy transfer and dissipation, and memory for recovery during radial distention.

This action resulting from the embedding minimizes fiber-to-fiber friction and maximizes kinetic energy dissipation, which is important in a continuously active in vivo structure. Uniform infusion provides a level of strength-to-elongation that would otherwise fail to yield to above-normal physical tension or internal hemodynamic pressure.

The infusion coating is generally greater than 10% by weight of the lumen and is cross-linked after coating to achieve a cross link density near thermoset. In some presently-preferred embodiments, the lumen is in the range of 15% to 35% by weight of the infused PGS elastic material, such as about 20% to about 30% by weight.

In some embodiments, the infusion coating may not readily penetrate the braid as a result of physical or chemical resistance to the wetting of the fibers by the infusion coating or the fiber bundles of the braid may be too tight for the infusion coating polymer to fully wet the bundle. As a preliminary step to the infusion coating process, the braids may be preconditioned in a surface-active treatment (e.g., a dip, bath, or ultrasonic infusion of a wetting agent solution or a simple solvent solution, etc.) to modify the fiber resin surface interaction and promote resin penetration via wetting agent or etching of and into the interstitial lattice network to pre-wet or surface modify the fiber and provide better infusion and surface contact of the polymer with the braid fibers.

Figure 3:
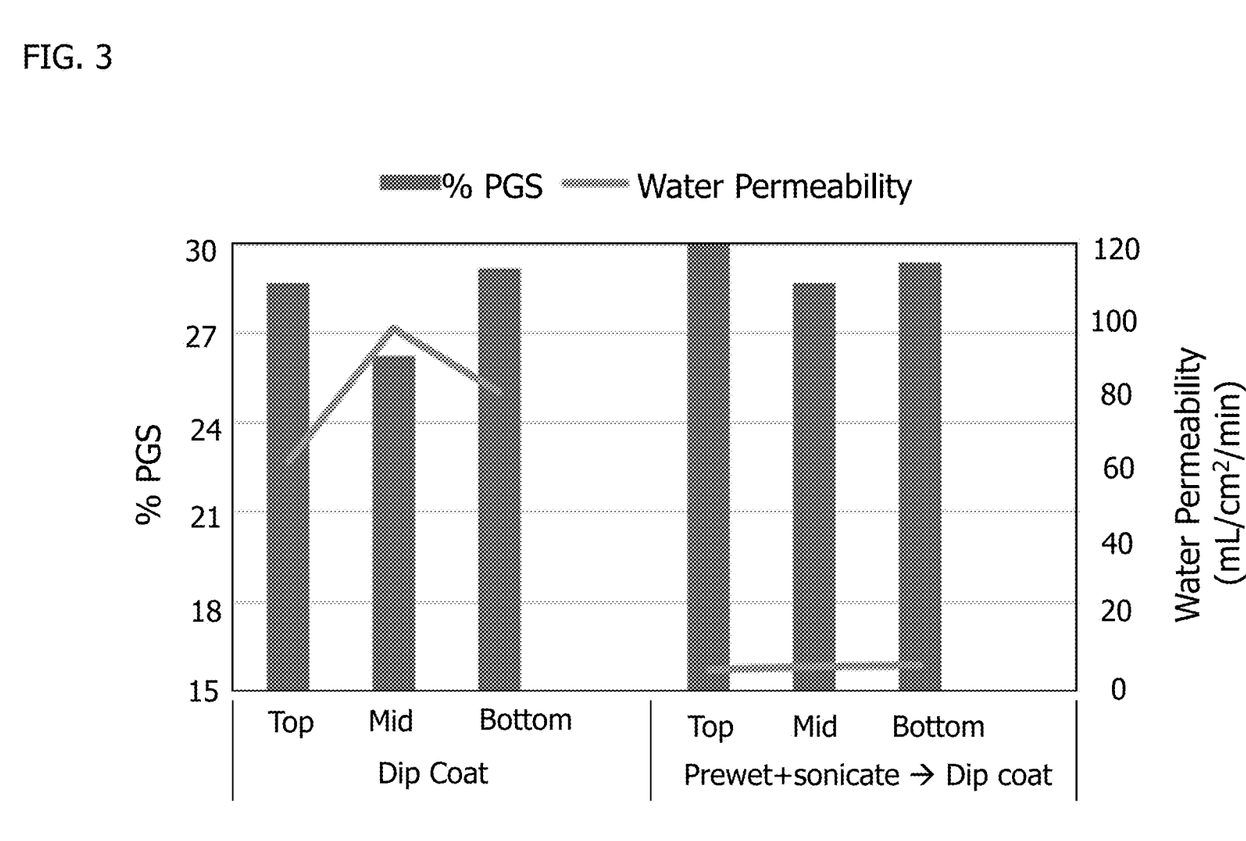
FIG. 3 shows the improvement in a PGS infusion coating of a braid with a prewet-and-sonicate preconditioning step.

FIG. 3 shows that a pre-wetting and sonication preconditioning step prior to dip coating significantly reduces the water permeability of the resulting PGS infusion coated braid. A dip coating without a previous pre-wet and sonicate step produced a coated braid having a water permeability in the range of about 60 to about 100 mL/cm$^2$/min). In contrast, by pre-wetting and sonicating prior to dip coating, the process gives a coated braid having a water permeability of only about 5 mL/cm$^2$/min or less.

Such preliminary treatments may eliminate "dry" or "hot" spots within the braid lattice, that is eliminate spaces within the bulk structure that have been excluded from the infusion process. This pre-treatment helps protect against premature failure from an aneurysm or blow-out from hemostatic pressure. Furthermore, the fibers themselves can be pre-treated prior to braiding. If the braided construct is scrubbed prior to manipulation, a wetting treatment may be incorporated into the scrubbing solution.

Preliminary treatments may include the use of wetting agents incorporated into the biodegradable polymer composition used to form the fiber of the braid and/or sheath/core technology to produce a selective wetting modification of the surface of the fibers during manufacture prior to braiding.

It will further be appreciated that braids may be plasma treated prior to infusion and that the braids may be exposed to ethylene oxide sterilization gas prior to coating to modify the surface to change the wetting action.

Other coating techniques for application of the infusion coating and/or any pretreatment coating include vapor deposition and infusion, as well as ultrasonic bathing of the braided structure in a wetting or polymer bath prior to the PGS infusion coating.

Braided structures in accordance with certain embodiments described herein have been successfully implanted into rats and pigs and remodeled into native vascular tissue, and composite braids made with these parameters may be water tight with a water permeability of 0 mL/cm$^2$/min and a kink radius of less than 10 mm.

According to another exemplary embodiment, the lumen structure is a crocheted lumen structure. Among the advantages of a crocheted lumen is the ability to form the lumen structure from a single yarn, including the possibility of the yarn as a single monofilament. Accordingly, there is a continuous thread throughout the article and even if one loop breaks, the structure remains stable. Crocheted lumens elongate and foreshorten, radially distend, and may be coated in the same manner as the braid, both with respect to the elastomeric infusion coating and with respect to any pre-treatments. Depending on the loop density, crocheted lumens may more readily accept an infused coating without pretreatment while still maintaining the uniformity of the inner and outer lumen walls.

Figure 4A:
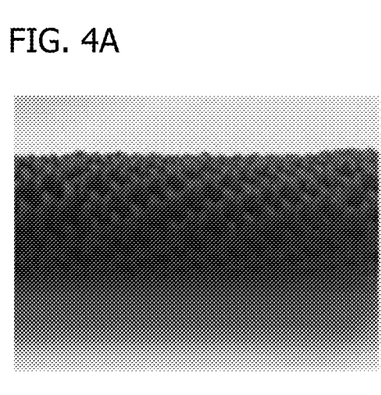
FIG. 4A shows a side view of a lumen formed by a continuous crochet action around a mandrel in an exemplary embodiment.
Figure 4B:
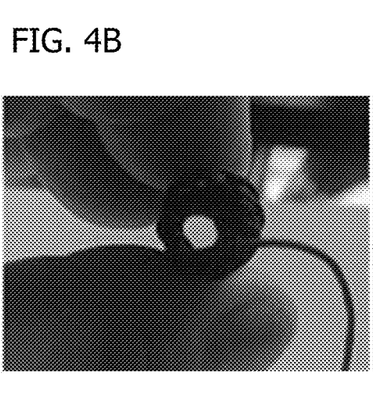
FIG. 4B shows an end view of the lumen of FIG. 4A.
Figure 4C:
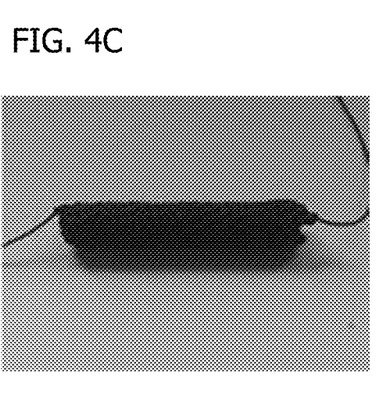
FIG. 4C shows a second side view of the lumen of FIG. 4A.

FIG. 4A, FIG. 4B, and FIG. 4C illustrate a lumen formed by a continuous crochet action around a mandrel. FIG. 4A shows the crochet pattern on the lumen. FIG. 4B shows the cylindrical opening of the lumen. FIG. 4C shows the two opposite ends of the single strand of yarn used to form the lumen extending from opposite ends of the lumen.

In some embodiments, a circular warp knit or a tubular double needle bar warp construction may be employed. Because they are both warp knit constructions (not weft knit), they have good stability and will not unravel when cut.

Additionally, the density and stretch properties are tunable by modifying pattern, yarn size, or course counts.

Figure 5:
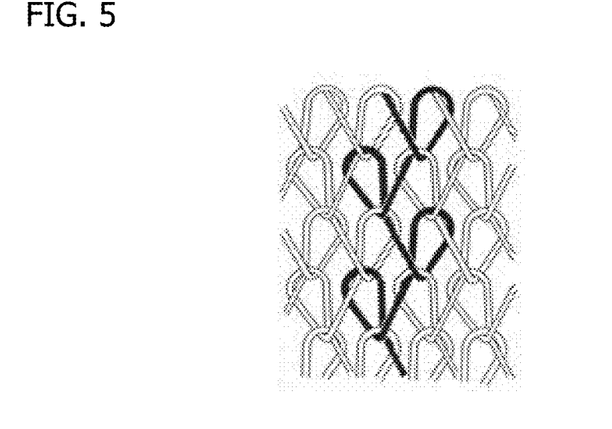
FIG. 5 shows the loop structure of a warp knitted structure in an exemplary embodiment.

Warp knitted structures are created using a continuous interlocking chain of loops, resulting in stable structures. Multiple fibers are combined together by the interlocking of loops along the length of the fabric being produced. The locking of these loops creates structure with both a high level of compliance and strength, as well as limiting material fraying and fabric runs. A warp knitted structure has an increased suture retention over a braided construction as a result of its inter-looping structure, as shown in FIG. 5.

Figure 6:
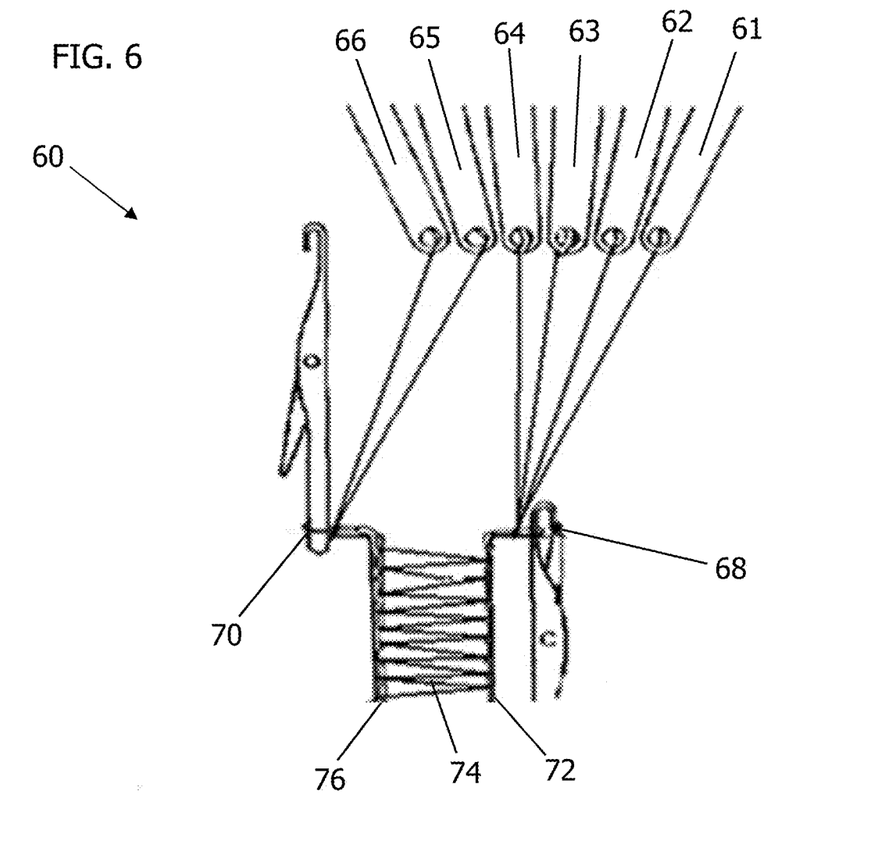
FIG. 6 shows a schematic profile of a double needle bar warp knitting machine in an exemplary embodiment.

In some embodiments, a double needle bar warp knitting machine 60, as shown schematically in FIG. 6, is utilized to create a hollow lumen structure with tunable properties, including, but not limited to, porosity, density, thickness, radial distension, and longitudinal stretch. The double needle bar warp knitting machine 60 includes a first guide bar 61, a second guide bar 62, a third guide bar 63, a fourth guide bar 64, a fifth guide bar 65, a sixth guide bar 66, a front needle 68, and a back needle 70 forming a front layer 72, a middle layer 74, and a back layer 76 of the fabric.

A double needle bar warp knitting machine has two needle beds, allowing it to create two independent fabric layers at one time as well as combine those two layers in specific areas. The double needle bar machine creates fabric layers that are then knit together on edges along the length, creating a continuous, in-line seam up the fabric and resulting in a hollow lumen structure. Double needle bar warp knitting machines have a large amount design flexibility, and features such as porosity, density, compliance, and stretch may be modified by changing knit pattern, machine gauge, and course counts within the knit fabric.

In some embodiments, a circular warp knitter is used to form a knitted fabric by interlocking loops of fibers together, giving it compliance, strength, and dimensional stability. A circular warp knitter operates similarly to a normal warp knitting machine but is limited by the pattern and density that are able to be created. However, an advantage of a circular warp knitter is the creation of a seamless tube, as the needles on the machine are arranged continuously around an actuating cylinder, as opposed to the double needle bar, which has two needle beds parallel to one another. Circular warp knitting design is a product of the size of the knit cylinder and the density of needles on the cylinder, resulting in new cylinders being needed based on density and diameter of the final knit construction.

According to another exemplary embodiment, a hollow lumen is prepared as an extruded composite tube. The tube is extruded from a composite composition including a PGS resin and small particles (e.g., particle sizes of less than 1000 microns) of a PGS thermoset filler material. The composite may be as described in U.S. Pat. App. Pub. No. 2017/0246316, incorporated herein by reference.

The matrix resin of the extruded tube is preferably selected to be able to flow or soften at a given temperature to allow for particle integration. Particularly in the case where the resin is PGS, the PGS resin preferably has a weight average molecular weight in the range of 5,000 to 50,000 Da. In some embodiments, the PGS resin has a weight average molecular weight in the range of 15,000 to 25,000 Da.

The matrix may be composed entirely of the polymer resin or may include one or more additional components. In some embodiments, the matrix contains one or more drugs, medicaments, or other biologically- and/or pharmaceutically-active ingredients, which may be incorporated therein for controlled release during subsequent resorption or degradation of the matrix due to the surface-eroding characteristics of PGS.

The thermoset PGS filler of the composite extruded tube has been processed into a flour or powder of fine particle size (e.g., less than 1000 microns). The PGS thermoset filler cross-link density is about 0.07 mol/L or greater, which is calculated with respect to the thermoset material prior to particularization by soaking samples in tetrahydrofuran for 24 hours to obtain a swollen mass, and then drying until a constant dry mass is acquired (typically about 3 days) and the swelling percentage is then used to calculate the cross-link density using the Flory-Rehner expression for tetra-functional affine networks. Filler particle size may vary, but in some embodiments the average particle size is in the range of about 75 to about 300 microns, such as, for example, about 175 to about 250 microns.

The molar ratio of glycerol:sebacic acid in the thermoset PGS used for the filler material may vary but typically is in the range of 0.7:1 to 1.3:1, with a preference in some embodiments for a 1:1 molar ratio. While the stoichiometric ratios of glycerol to sebacic acid may be varied for the PGS particles, the particles should still be of a surface energy similar to that of the resin matrix. For example, a composite that includes a PGS thermoset filler made from 1:1 glycerol:sebacic acid molar ratio may be dispersed in a PGS resin matrix that also has a 1:1 glycerol:sebacic acid molar ratio.

The weight percentage of filler in the composite ranges from about 10% by weight to about 90% by weight filler, typically about 40% by weight to about 70% by weight filler, and the resulting composite is then extruded to form a tube using a Brabender or fiber extrusion or other suitable extrusion device to form tubes having any suitable outer diameter. Exemplary embodiments have shown to be particularly useful with small outer diameters, such as those having an outer diameter of about 6 mm or less, such as between 2 and 4 mm, such as about 2.5 mm or about 3.0 mm.

While the lumen may be useful in its initially-extruded form, in some embodiments an overbraid is applied following extrusion in which fibers of a bioresorbable material (PGA, PLA, PLGA, PGS, etc.) are braided overlying the exterior surface of the tube. The addition of the braid may aid in providing increased burst strength, kink resistance, and stability to the extruded tube and thus a superior result in the resulting lumen. Instead of an overbraid, the overlying layer applied surrounding the extruded tube may also be a crochet or knit textile.

The overbraid is a separate layer formed around the extruded tube surface. In some embodiments, the overbraid is heat-set to retain its shape even when the lumen is cut or manipulated. In other embodiments, the lumen is dip coated to physically connect the overbraid with the extruded tube. By dip coating, the overbraid maintains its morphology without heat setting and is then secured to the underlying extruded tube. In some embodiments, the lumen is dip coated in PGS or other bioresorbable resin that infiltrates some of the space within the braid, such that upon curing of the dip coated resin, the overbraid is laminated to the underlying tube. Additional advantages of applying PGS resin to the overbraid include reducing potential for inflammation from the textile and decreased adhesion formation.

Figure 7A:
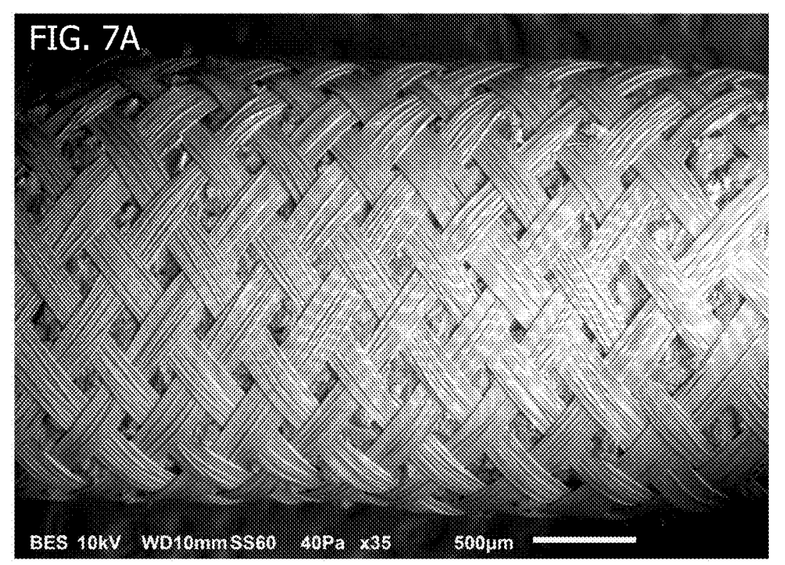
FIG. 7A shows a side view of an extruded PGS tube with a polyglycolide (PGA) overbraid in an exemplary embodiment.
Figure 7B:
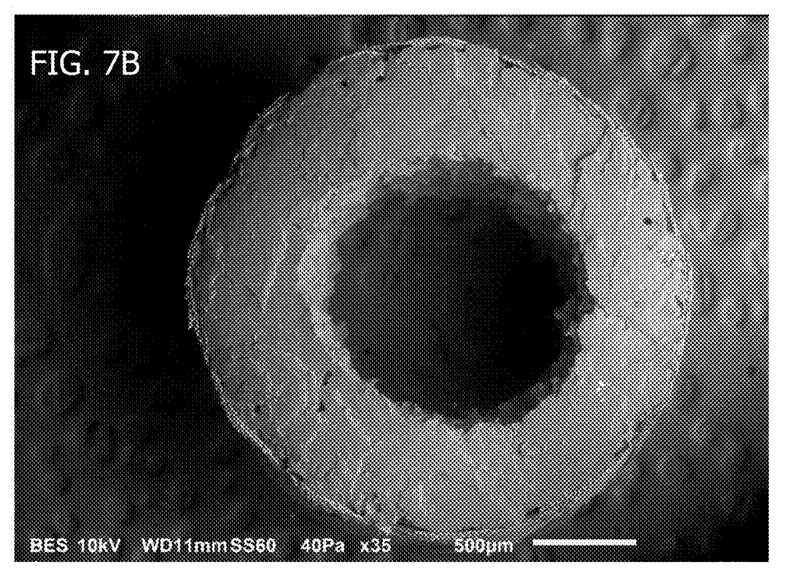
FIG. 7B shows an end view of the extruded PGS tube with the PGA overbraid of FIG. 7A.

FIG. 7A and FIG. 7B illustrate a lumen formed by extrusion followed by application of an overbraid. FIG. 7A shows the overbraid pattern with parts of the lumen visible through the overbraid. FIG. 7B shows the cylindrical opening of the lumen and the relative thicknesses of the lumen and the overbraid.

In order to impart structural support while maintaining flexibility of the extruded tube, the overbraid braiding parameters may differ from those described in earlier embodiments. For a 2.5-mm outer diameter extruded tube, the overbraid braiding parameters may include an overbraid braid angle in the range of 75 to 151, such as 100 to 120, a PPI in the range of 30 to 150, such as 40 to 80, 24 to 36 ends, a 1×1 braid pattern, or an effective yarn denier in the range of 45 to 90.

The wall thickness of the extruded tube for a 2.5-mm outer diameter may range from 200 μm to 1200 μm in thickness, preferably from 200 μm to 500 μm thick. It will be appreciated that as the extruded tube wall thickness decreases, the overbraid braiding parameters may be adjusted to provide more structural support while maintaining flexibility of the tube. It will further be appreciated that wall thickness may change as outer diameter increases beyond 2.5 mm, although in most embodiments the thickness should not increase beyond the point at which the tube loses flexibility.

These embodiments have been reduced to practice and were the subject of small-diameter arterial tissue-engineered vascular graft (TEVG) in a rat model of infrarenal abdominal aorta interposition grafting. Extruded grafts were fabricated of PGS with some embodiments having a PGA braid over the extruded lumen. A total of 30 cases were implanted, with 5 cases in each group evaluated at one month and 10 cases in each group evaluated at three months.

At one month, remodeled grafts displayed an endothelial cell monolayer, contractile vascular smooth muscle cells, extracellular matrix (ECM) deposition, and macrophage infiltration, without any incidence of graft dilatation or rupture. The inner diameter, wall thickness, elastin thickness, ECM area, and total number of macrophages (based on $CD68^+$) in the remodeled grafts were measured, and there was no significant difference between the two groups except for in wall thickness of the remodeled graft. These results reflect that exemplary embodiments using an extruded lumen lead to the formation of well-organized vascular neotissue without aneurysm or graft rupture at one-month follow-up.

At three months, the extracellular matrix (ECM) deposition and the inner diameter and wall thickness of the braid grafts were comparable to that of native aorta. Both graft types demonstrated 10% calcified area at 3 months due to the remaining scaffold. The data suggests that the PGS-extruded grafts degrade rapidly to lead to rich cellular infiltration, but mechanical support such as implementation of PGA braided technology may be needed to induce ECM formation and prevent graft dilatation over time.

In another embodiment, the exterior and/or the interior of the extruded lumen embodiments may be coated following extrusion, such as by dip coating, or, in some embodiments, may be co-extruded with an outer shell of another material. In some embodiments, only the exterior surface is coated to permit intimate contact of the inner lumen surface with cells with the PGS material and thus encourage regeneration of native tissue to begin at the inner wall of the conduit.

The coating may be applied over the extruded lumen, over the over-braided structure applied to the extruded lumen, or both, with the lumen being plugged prior to application of the coating if a coating on the interior surface is to be avoided. In some embodiments, the coating is a urethane coating that may be achieved, for example, by dipping, spraying or otherwise applying an isocyanate. The isocyanate may be an aliphatic isocyanate, such as, for example, hexamethylene diisocyanate (HDI), but in some embodiments may instead be an aromatic isocyanate, such as toluene diisocyanate (TDI) or methylene diphenyl isocyanate (MDI), again by way of example. The use of a urethane or other outer coating may further enhance burst strength and/or suturability.

While described primarily herein with respect to lumens constructed to achieve properties suitable for use as a vascular graft, the invention is not so limited and other graft constructions may also be created, as well as any other tissue vessel that is necessary to be resected and replaced and which in turn supports endogenous regeneration of native tissue.

For vascular grafts, exemplary embodiments may be employed for use as coronary artery bypass grafts, arteriovenous grafts, cerebral artery bypass grafts, pediatric shunts such as Blalock-Taussig (BT) shunts and sano shunts, peripheral grafts such as femoral-popliteal bypass, femoral-femoral bypass, aortic-bifemoral bypass, axillary-bifemoral bypass, femoral-tibial bypass, and dorsalis-pedis bypass.

Diseases/conditions where lumens in accordance with exemplary embodiments may be employed may include, but are not limited to, any of coronary artery disease, cardiac aneurysm, hypertension, cardiac stroke, vascular aneurysm, kidney failure, vascular occlusion, diabetes, and organ transplantation.

In addition to grafts, other tubular tissues for which lumens in accordance with exemplary embodiments may be employed include, for example, nerve guide and conduit tissues, lymphatic vessels, gastrointestinal tract tissues, and urogenital tract tissues, including the ureter, vas deferens, and fallopian tubes.

It should be understood that while the invention has been described with reference to one or more embodiments, various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention. In addition, all numerical values identified shall be interpreted as though the precise and approximate values are both expressly identified.

What is claimed is:

1. A composite lumen comprising:
   an extruded tube of a composite comprising a poly (glycerol sebacate) (PGS) matrix mixed with a PGS thermoset filler; and
   an overbraid structure overlying an outer surface of the extruded tube.

2. The composite lumen of claim 1 wherein the PGS thermoset filler comprises a powder of thermoset PGS having an average particle size in the range of about 75 to about 300 microns.

3. The composite lumen of claim 1, wherein the PGS thermoset filler is present in an amount in the range of 10% to 90% by weight of the extruded tube.

4. The composite lumen of claim 1, wherein the overbraid structure comprises fibers of a bioresorbable material.

5. The composite lumen of claim 4, wherein the bioresorbable material is selected from the group consisting of polyglycolide, polylactide, poly(lactic-co-glycolic acid), poly(caprolactone) and PGS.

6. The composite lumen of claim 1, wherein the overbraid structure is laminated to the extruded tube.

7. The composite lumen of claim 1, wherein the extruded tube has an inner diameter of less than 6 mm.

8. The composite lumen of claim 1, wherein the overbraid structure has an overbraid angle in the range of 75° to 151°.

9. The composite lumen of claim 1, wherein the overbraid structure has a picks per inch in the range of 30 to 150.

10. The composite lumen of claim 1, wherein the overbraid structure has a 1×1, 2×2, or 2×1 braid pattern.

11. The composite lumen of claim 1, wherein the overbraid structure has an effective yarn denier in the range of 45 to 90.

12. The composite lumen of claim 1, wherein the extruded tube has a wall thickness in the range of 200 μm to 1200 μm.

13. A method of forming a composite lumen tube, the method comprising:

extruding a poly(glycerol sebacate) (PGS) tube of a composite comprising a PGS matrix mixed with a PGS thermoset filler; and     applying an overbraid structure over an outer surface of the extruded tube.

14. The method of claim 13 further comprising mixing the PGS matrix with the PGS thermoset filler prior to extruding the PGS tube.

15. The method of claim 13 further comprising heat-setting the overbraid structure after applying the overbraid structure.

16. The method of claim 13 further comprising dip coating the composite lumen tube after applying the overbraid structure to physically connect the overbraid structure with the overbraid structure.

17. The method of claim 13, wherein the PGS matrix comprises a PGS resin having a weight average molecular weight in the range of 5,000 to 50,000 Da and the PGS thermoset filler comprises a powder of thermoset PGS having an average particle size in the range of about 75 to about 300 microns.

\* \* \* \* \*